Figure 1:
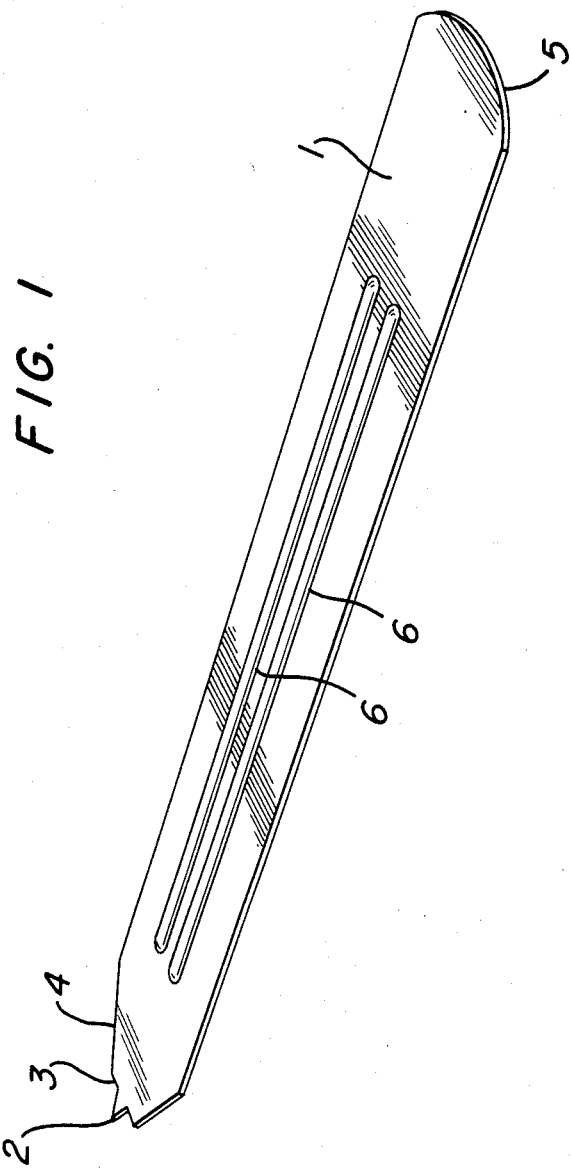

United States Patent [19]
Gullberg

[11] Patent Number: 4,714,621
[45] Date of Patent: Dec. 22, 1987

[54] COATING METHOD
[75] Inventor: Carl E. Gullberg, Storvreta, Sweden
[73] Assignee: Pharmacia AB, Upsala, Sweden
[21] Appl. No.: 946,512
[22] PCT Filed: Apr. 8, 1986
[86] PCT No.: PCT/SE86/00157
  § 371 Date: Dec. 2, 1986
  § 102(e) Date: Dec. 2, 1986
[87] PCT Pub. No.: WO86/06268
  PCT Pub. Date: Nov. 6, 1986
[30] Foreign Application Priority Data
  Apr. 24, 1985 [SE] Sweden .................................. 8501990
[51] Int. Cl.$^4$ .......................... A01N 1/02; B05D 3/12; A61B 15/00
[52] U.S. Cl. ........................................ 427/2; 128/743; 427/327
[58] Field of Search ...................... 128/743; 427/2, 327

[56] References Cited
FOREIGN PATENT DOCUMENTS
2940342 4/1979 Fed. Rep. of Germany .
 315464 9/1969 Sweden .
2117247 10/1983 United Kingdom .

*Primary Examiner*—Michael R. Lusignan
*Attorney, Agent, or Firm*—Fred Philpitt

[57] ABSTRACT

Method for applying a coating of allergen on a steel tip of an instrument which is to be employed for in vivo allergy diagnostication and which has stop means adjacent to the steel tip so that solely said tip can penetrate the skin. The characteristic feature of said method is that the steel tip plus those portions of the stop means that lie in the immediate proximity of said tip are acid-pickled and then coated with allergen, to thus cause an active amount of allergen to adhere to said tip.

1 Claim, 1 Drawing Figure

COATING METHOD

TECHNICAL FIELD OF THE INVENTION

The invention relates to a method for applying a coating of allergen on the tip of an instrument, which is to be employed for in vivo allergy diagnosis, so-called prick tests on skin.

In the present specification and claim, the term "allergen" refers to a substance capable of causing an allergic reaction, unless stated otherwise.

STATE OF THE ART

In vivo allergy diagnosis is a means of identifying the specific allergen(s) to which a patient is allergic, the technique of this diagnostication involving the following procedure: A drop of allergen extract or of allergen in some other suitable form is deposited on the skin. Thereafter, the skin is punctured by means of the tip of a cannula, or with a needle, lancet or other pointed tool, to thus cause the allergen to penetrate into the skin where the allergen then may give rise to an allergic reaction; for instance, the allergen may react with IgE antibodies bound to mast cells which release inflammatory mediators. The technique as such is well known and is described in numerous textbooks and review articles (see for example Allergy and Clinical Immunology, Grune & Stratton Inc., 1976, p. 164–170).

The instruments employed for puncturing may take various forms and shapes. Thus, for instance, special needles have been employed, which are made of steel and have a tip configuration optimized for skin testing (Malling, J-J et al., Allergy 37 (1982), p. 563–67). When such a needle is to be employed, an excess of allergenic material is deposited on the skin, whereupon puncturing is effected by means of the needle, and the residual excess of allergen is then wiped off. Needles that have been coated with allergenic substances prior to their use in prick testing have also been proposed as suitable tools. For instance in No. DE-A-2,940,342, a lancet is described, onto the tip of which a drop of an allergenic preparation is deposited, freezed and lacquered prior to use. Neither pickling in general nor acid pickling as a pretreatment step is discussed.

The techniques employed at present for carrying out this type of tests have several disadvantages among which may be mentioned, for example, operators working with these tests run the risk of becoming sensitized and that difficulties arise in comparing results from tests of different dates, these latter disadvantages being i.a. due to the difficulty of causing a standardized amount of allergen to reproducibly penetrate the skin. Moreover, it may turn out to be difficult to compare results obtained with different species of allergens. Also, in accordance with methods commonly employed at present, an excess of allergen is applied and then afterwards wiped off. This means that on each occasion comparatively large amount of expensive material is being used up.

The object of this invention is to minimize these disadvantages, i.e. to increase the reproducibility of test results obtained variously at different times and with different allergen preparations of either the same or different allergens. The invention, moreover, is aimed at reducing sensitization hazards for patients and for personnel carrying out the tests.

As far as we know, earlier attempts at reproducibly coating the metal tip of the puncturing instruments have failed, mainly because no insight had been gained into the nature of the factors governing the adherence of allergenic substances to metal objects. An important point to be noted is that the allergenicity of the allergenic substance must not be destroyed. From the instrument the substance must be transferrable in a potent form to the skin of the patient to be tested. In addition, it is a requirement that the substance remains in place on the tip of the needle until the instrument is actually applied in the desired manner. If the substance becomes disengaged from the tip too soon this will involve a great risk that the result obtained turns out to be nonreproducible, plus the risk that the person performing the test is exposed to an increased sensitization hazard. A factor affecting the adhesiveness of the allergen preparation is its origin and composition. Thus allergen preparations rich in polysaccharides, e.g. from molds and plants, have a relatively high degree of adhesiveness to steel surfaces; whereas others which are poor in polysaccharides, e.g. mammalian epithelia, possess only little adhesiveness to steel surfaces. As a rule the allergenic component is always a protein and the degree of its adhesiveness is determined by the other components present in the preparation. A second factor is the luster of the steel, i.e. its surface depth. As a rule an increased surface depth is conducive to improved adhesion. A third factor may be impurities, if present, such as e.g. fat and metal oxides. Impurities may involve a substantial deterioration of adhesiveness. It will thus be appreciated that there are a number of factors which are decisive for the allergenic activity of an allergen preparation when that preparation adheres to a steel tip.

THE INVENTION

The invention provides a method by which due consideration is given to these factors so that the entire tip of the puncturing instrument can be coated with a reproducible and standardized active amount of allergenic substance. This is achieved by acid pickling of the tip prior to the coating thereof.

On any two given tips the pickling must be carried out under exactly the same conditions if the results obtained with these tips are to be comparable inter se. Pickling according to the invention has the effect that the steel surface of a tip is cleansed from oxides and other impurities, and presumably also has the further effect that the microstructure of the steel surface is affected favourably for coating with an active amount of an allergenic substance. Fat-soluble materials are removed from the steel prior to pickling, in that the surface to be pickled is treated with a fat-dissolving substance such as, for instance, trichloroethane.

The statement that an active amount of material is to be present on the tip means that a local allergic reaction will result upon puncturing of the skin of an allergic individual with the tip. The active amount expressed in grams varies among different allergen preparations of the same allergen as well as among different types of allergens. Normally the tip is covered with an amount of allergen (protein) within the range of 0.1–10000 ng, in particular 8–1000 ng. The activity may be expressed as biological units, B.U. (Nordic Guidelines, Publ. No. 7, Chapter 3.4.2 Biological Potency; Nordic Council of Medicine, Uppsala, Sweden), and according to the invention the lancet tip is coated with an amount of allergen such that the reaction in the skin when the allergen is used will correspond to $10^4$–$10^6$ B.U., as e.g. $10^5$ B.U. The wide range of variations in specific activity liable to occur with different types of allergen is exemplified in Table 1.

| Allergen activity | |
|---|---|
| Species | Specific activity mg/100,000 B.U. |
| English ryegrass | 0.04 |
| Timothy | 0.18 |
| Alder | 0.04 |
| Birch | 0.75 |
| Hazel | 0.15 |
| Cat | 0.72 |
| Horse | 0.98 |
| Dog | 1.72 |
| Mugwort | 0.26 |
| *Cladosporium hebarum* | 4.35 |
| *Alternaria tenuis* | 4.00 |
| *Dermatophagoides pteronyssinus* | 1.03 |
| *Dermtophagoides farinae* | 1.03 |

DESIGN OF THE INSTRUMENT

The instrument may be embodied in various different forms, the most critical feature being the shape of the tip. In the present specification and claims "tip" means that portion of the instrument which will penetrate into the skin upon puncturing thereof. According to a very advantageous embodiment the tip is given a shape such that puncturing of the skin is effected reproducibly to a suitable depth; for in this context it should be noted that the local allergic reaction obtained will depend on i.a. the depth of the puncture and the angle at which puncturing is effected. The instrument may take the form of a lancet, the tip of which has shoulders, and the handle of which has been given a shape such that the test operator will always prefer to puncture the skin at the same angle, for example 45° or 90° (measured between the skin and the instrument). The shoulders effectively act as stop means so that only the tip can pierce the skin. An advantageous embodiment is shown in FIG. 1. In that FIGURE, a puncturing instrument is shown which has the shape of a lancet. It consists of a plate (1) which is substantially rectangular and oblong. On one of its short sides it has a tip (2), preferably triangular, the base of the tip attaching to the short side in a manner such that the tip at right angles in the plane of the plate projects therefrom. It is recommendable that the plate and tip are punched from the same sheet of metal (stainless steel). The portion of the short side surrounding the tip base forms two means (3) which can be made to penetrate the skin with only the greatest difficulty. These means are called "shoulders" or "stop means" and are directed substantially at right angles outward from the longitudinal axis of the instrument. The corners (4 and 5) of the plate may be beveled for the sake of optimum grip and esthetic appeal. In the longitudinal direction of the plate longitudinally extending ridges or recesses=- grooves (6) may be embossed/impressed in the plate. These will thwart accidental folding or bending of the instrument. The exact dimensions of the instrument are determined by practical considerations. For example, the length of the instrument is chosen such that the tip can easily be handled to penetrate the skin at a given angle, for instance at 90°. The length may be in the range of 25-45 mm, and the width in the range of 3-6 mm. The ratio of the depth of the tip to the width of one stop means may vary from e.g. 0.1 to 1.

As regards the visual appearance of the tip, this may vary within wide limits. Examples of different embodiments are plainly neddle-shaped and triangular tips, hollow tips, and tips formed with a surface-increasing scallops configuration. If the surface is increased, this means that a larger area is at one's disposal for coating, i.e. the tip can be coated with a larger amount of allergen. If the tip is formed with surface-increasing features, these must be chosen such that they will not negatively affect the possibilities of performing reproducible and painless punctures of the skin. A triangular tip is a preferred embodiment.

According to the invention, the surface which is to be coated with the allergen should be made of stainless steel, an important proviso being that the steel should be of a quality such as to minimize the risk of the test person's becoming sensitized to metal. The other, non-coated portions of the instrument may preferably be of the same material although they may also be made of other material.

Coating of the tip

The invention utilizes acid pickling with the aid of a mineral acid such as, for instance, hydrochloric acid, sulfuric acid or mixtures thereof. The degree of efficiency of the pickling will depend on the concentration of the acids and on the time during which the steel is exposed to the treatment. An average expert will easily find out suitable conditions. Treating periods that are too long or concentrations that are too high will tend to bring about dissolution of the steel. If, on the other hand, the treating periods are too short or the concentrations are too low, the thus resultant pickling will be of an inferior quality, so that the allergen will exhibit poor adhesiveness. Various additions of salts, such as sodium chloride, may increase the pickling capacity of a pickling bath. Oxidizing acids in a concentrated form, such as e.g. nitric acid, are conducive to poor pickling, whereas additions of soluble salts of non-oxidizing mineral acids may increase the pickling capacity of nitric acid (oxidizing acid). Particularly good results have been obtained with aqueous hydrochloric acid solutions having concentrations of from 3M upwards; the acid has been diluted in water or concentrated nitric acid.

After the pickling step the tip is rinsed, whereupon the rinsed surface before being recontaminated is coated with allergenic material. This may be done by contacting the tip with a preparation of standardized allergen, preferably an aqueous solution thereof, the concentration of this standard material being for example 0.004–0.4 mg/ml. Thereafter the tip is dried (optionally freeze-dried). The instrument thus dressed and ready may advantageously be stored in a vacuum, with the exclusion of air and moisture. Coating is performed aseptically to make sure that a sterile product is obtained. When the pickling is carried out, care is to be taken that the portions of the stop means lying in the immediate proximity of the tip of the instrument are pickled and coated with allergen. In this manner a reproducible coating of the tip is ensured.

The invention will now be further exemplified by means of a number of non-limitative patent examples.

EXAMPLE 1

Manufacture of instruments

A. Pickling

A number of lancets (Swedish high-grade steel, Sandvik AB, Sweden) are introduced into a system of hangers from which each lancet hangs down freely. From these lancets any rests of fat are washed off by means of trichloroethane. The hanger system is then suspended in a rack over a bath containing HCl 5M so that each lancet tip plus a few millimeters up the shoulder will come into contact with the liquid. After seven minutes, pickling is discontinued and the lancets are washed carefully in distilled water until all of the residual hydrochloric acid has been removed. Then the lancets are dried and sterilized in a hot cabinet.

Acceptable results are also obtained if pickling is carried out at other concentrations and with mixtures of mineral acids. In these cases pickling times may have to be varied. Experiments of this type have been carried out and are listed in the below Table. Whenever clinical test results from tests made with a plurality of lancets are to be compared inter se it is a prerequisite that these lancets have all been pickled under identical conditions.

| | Pickling of steel material | |
|---|---|---|
| Acid | Concentration | Time |
| $HNO_3$ + NaCl | conc. | 15 min. |
| $HNO_3$/HCl | conc. 2:1 | 2 sec. |
| $HNO_3$/HCl | conc. 5:1 | 2 sec. |
| $HNO_3$/HCl | conc. 5:1 | 30 sec. |
| HCl | conc. | 1–5 min. |
| HCl | 5 M | 1–10 min. |

If the duration of the treatment is too long the lancets tend to assume a brownish colour, which is esthetically unsatisfactory. The pickling according to the invention should give lancets free of miscolouring.

B. Coating with allergen 40 sterilized lancets (pickled as according to 1 A) are suspended on hangers so that they are all on the same level. A sterile solution, X ml, of the allergen English ryegrass (Allergon AB, Sweden) is prepared, at a concentration of 0.04 mg/ml. The lancets are then transported laterally so as to pass over the solution, each lancet being allowed to contact with this allergen solution for 0.5 minute; in this manner allergenic material is caused to adhere to the lancet. Next the lancets are dried in LAF (Laminal Air Flow) for about 5 minutes, whereupon they are packed aseptically in moisture-proof casings. With the aid of immunoelectrophoresis it is possible to evaluate the amount of allergen attaching to the lancet semiquantatively.

EXAMPLE 2

Prick tests with lancets

The lancet casing is opened. The lancet is seized by the upper part of the handle and is directed at right angles to the skin (forearm underside, or back) whereupon the skin is pierced by means of a light pressure on the lancet which is then immediately retracted and discarded. If several tests are carried out simultaneously there should be a distance of at least 2 cm between punctures. After 15 minutes the skin reaction is read off. An erythema and a wheal can be seen if the patient has reacted positively. The size of the wheal is proportional to the reactivity of the patient. Prick tests have been performed both with pickled and non-pickled lancets; it was found that a pickled lancet is coatable with a higher amount of allergen activity than a non-pickled lancet (the comparison being made using the same allergen preparation in each case). With the aid of comparative prick tests the coating method of this invention has been calibrated for each allergen so that each lancet tip can be coated with 100,000 B.U. of allergen.

I claim:

1. In a method for applying a coating of allergen on a steel tip of an instrument which is to be employed for in vivo allergy diagnostication and which has stop means adjacent to the steel tip so that solely said tip can penetrate the skin, the improvement that the steel tip plus those portions of the stop means that lie in the immediate proximity of said tip are acid-pickled and then coated with allergen to thus cause an active amount of allergen to adhere to said tip.

* * * * *